United States Patent
Kleiner

[11] Patent Number: 5,847,184
[45] Date of Patent: Dec. 8, 1998

[54] PROCESS FOR PREPARING PHOSPHORUS-CONTAINING DICARBOXYLIC ACIDS

[75] Inventor: Hans-Jerg Kleiner, Kronberg, Germany

[73] Assignee: Hoechst Aktiengesellschaft, Frankfurt am Main, Germany

[21] Appl. No.: 532,114

[22] Filed: Sep. 22, 1995

[30] Foreign Application Priority Data

Oct. 10, 1994 [DE] Germany .......................... 44 36 079.7

[51] Int. Cl.⁶ .......................... C07F 9/6571; C07F 9/141; C08G 63/692
[52] U.S. Cl. .......................... 558/73; 558/134; 528/287; 528/398
[58] Field of Search .................... 528/287, 398; 558/73, 134

[56] References Cited

U.S. PATENT DOCUMENTS

| | | | |
|---|---|---|---|
| 4,127,590 | 11/1978 | Endo et al. | 260/346.74 |
| 4,157,436 | 6/1979 | Endo et al. | 528/167 |

FOREIGN PATENT DOCUMENTS

| | | | |
|---|---|---|---|
| 2141258 | 7/1995 | Canada | C07F 9/53 |
| 665 237 | 8/1995 | European Pat. Off. . | |
| 2387276 | 11/1978 | France . | |
| 2642218 | 3/1977 | Germany . | |
| 2816100 | 10/1978 | Germany . | |
| 2646218 | 10/1980 | Germany . | |
| 2816100 | 8/1989 | Germany . | |
| 52-144627 | 12/1977 | Japan . | |
| 1575157 | 9/1980 | United Kingdom . | |

*Primary Examiner*—Joseph McKane
*Assistant Examiner*—Jane C. Osowecki
*Attorney, Agent, or Firm*—Connolly and Hutz

[57] ABSTRACT

The present invention relates to a process for preparing of phosphorus-containing dicarboxylic acids of the formula (I)

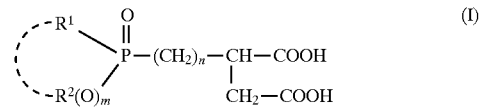

where $R^1$ and $R^2$ are identical or different and are each a straight-chain or branched alkyl radical having from 1 to 8 carbon atoms, a cycloaliphatic radical having 5 or 6 carbon atoms in the ring, an unsubstituted or substituted aryl radical having from 6 to 10 carbon atoms, or $R^1$ and $R^2$ form, with inclusion of the phosphorus atom, a ring having from 5 to 8 members, and m and n are each, independently of one another 0 or 1, by reacting a compound of the formula (II)

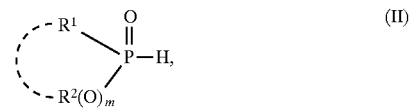

where $R^1$, $R^2$ and m are as defined above, with fumaric acid, maleic acid or itaconic acid in the presence of a saturated aliphatic monocarboxylic acid having a total of from 1 to 5 carbon atoms as solvent at from 100° to 200° C. under atmospheric pressure or superatmospheric pressure.

11 Claims, No Drawings

PROCESS FOR PREPARING PHOSPHORUS-CONTAINING DICARBOXYLIC ACIDS

The present invention relates to a process for preparing phosphorus-containing dicarboxylic acids which is improved in comparison with the prior art.

Phosphorus-containing dicarboxylic acids are valuable building blocks for the production of polymeric plastics. If phosphorus-containing dicarboxylic acids are used as comonomers, for example, in the preparation of polyesters, flame-resistant polyesters can be obtained (DE-C 26 46 218). Furthermore, phosphorus-containing dicarboxylic acids can be used for producing resin compositions having a flame-retardant action (DE-C 28 16 100).

Such phosphorus-containing dicarboxylic acids are obtained by performing a molecular addition of a suitable phosphorus-containing compound, for example 6H-dibenz-[c,e][1,2]-oxaphosphorin-6-one, to fumaric acid, maleic acid or itaconic acid. The molecular addition is carried out by mixing the starting materials and heating the resulting mixture to temperatures of from 100° to 250° C. However, in carrying out the reaction, difficulties occur in maintaining the correct temperatures, particularly in the case of an exothermic reaction. In addition, there are problems with handling the end product, since this is formed as a glass-like melt.

To circumvent these difficulties, it has also been proposed that dimethyl sulfoxide be used as solvent (DE-C 28 16 100, Example 1). However, in this process variant there is likewise an undesired exothermic reaction which, owing to an uncontrolled liberation of heat, prevents controlled maintenance of temperatures. In addition, after cooling the reaction mixture, there are also difficulties in isolating the desired end product. As shown by the comparative example given in the experimental part, the desired end product does not crystallize from the reaction mixture.

Accordingly, there is a need to develop a process for preparing phosphorus-containing dicarboxylic acids which eliminates the abovementioned disadvantages and can be implemented industrially without great expense and using readily available auxiliaries. In addition, the process should make the desired products available both in high yield and in high purity.

This object is surprisingly achieved by a process for preparing phosphorus-containing dicarboxylic acids of the formula (I)

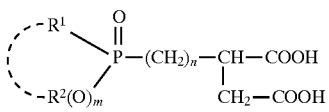

where $R^1$ and $R^2$ are identical or different and are each a straight-chain or branched alkyl radical having from 1 to 8 carbon atoms, a cycloaliphatic radical having 5 or 6 carbon atoms in the ring, an unsubstituted or substituted aryl radical having from 6 to 10 carbon atoms, or $R^1$ and $R^2$ form, with inclusion of the phosphorus atom, a ring having from 5 to 8 members, and m and n are each, independently of one another 0 or 1. It comprises reacting a compound of the formula (II)

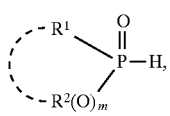

where $R^1$, $R^2$ and m are as defined above, with fumaric acid, maleic acid or itaconic acid in the presence of a saturated aliphatic monocarboxylic acid having a total of from 1 to 5 carbon atoms as solvent at from 100° to 200° C. under atmospheric pressure or superatmospheric pressure.

The reaction proceeds, for the example of maleic acid, according to the following equation

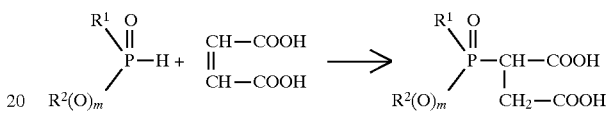

It is to be regarded as surprising that when carrying out the process of the invention an uncontrollable exothermic reaction can be avoided and, after the reaction is complete, the desired phosphorus-containing dicarboxylic acids generally crystallize from the reaction mixture formed and are here obtained in high and sometimes in excellent purity.

If desired or necessary, the solvent used can be distilled off and the mixture thus formed be crystallized.

However, the end products are frequently formed directly in such a purity as is necessary for direct use of the phosphorus-containing dicarboxylic acid as comonomer for preparing flame-resistant polyesters. In these cases, an additional purification step is no longer required.

In the preparation of cyclic compounds of the formula (I), it has been found useful to use compounds of the formula (II) in which $R^1$ and $R^2$ form, with inclusion of the phosphorus atom, a ring having 6 or 7 members. At this point it may be mentioned, for the sake of completeness, that the oxygen atom, if present (m=1), is counted as a member of the ring.

In many cases it has been found to be useful to use a compound of the formula (II) in which $R^1$ and $R^2$ are identical or different and are each a straight-chain or branched alkyl radical having from 1 to 4 carbon atoms, a cyclopentyl or cyclohexyl radical, an aryl radical which is substituted by one or more halogen, alkyl, alkoxy or aryl radicals, or $R^1$ and $R^2$ form, with inclusion of the phosphorus atom, an unsubstituted or substituted oxaphosphorin ring.

Also of interest are compounds of the formula (II) in which $R^1$ and $R^2$ are identical and are each a phenyl radical or a phenyl radical substituted by one or two alkyl groups or alkoxy groups each having from 1 to 4 carbon atoms and m=0.

Well suited starting materials are compounds of the formula (II) containing an oxaphosphorin ring. In particular, the compound of the formula (II) containing an oxaphosphorin ring which is used is a compound of the formula (III)

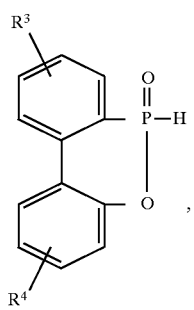

where $R^3$ and $R^4$ are identical or different and are each halogen, an alkyl radical having from 1 to 4 carbon atoms or an alkoxy radical having from 1 to 4 carbon atoms.

Without claiming completeness, suitable compounds of the formula (II) which may be mentioned are 6H-dibenz-[c,e][1,2]-oxaphosphorin-6-one, dimethylphosphine oxide, methylpropylphosphine oxide, diisopropylphosphine oxide, d-n-butylphosphine oxide, methylphenylphosphine oxide, diphenylphosphine oxide or di-p-tolylphosphine oxide.

The process of the invention is particularly suitable for reacting the compound of the formula (II) with itaconic acid, giving compounds of the formula (I) in which n=1.

Usually, the fumaric acid, maleic acid or itaconic acid and the compound of the formula (II) are used in a stoichiometric ratio or the fumaric acid, maleic acid or itaconic acid is used in a certain excess, based on the compound of the formula (II). It is advisable to use the fumaric acid, maleic acid or itaconic acid and the compound of the formula (II) in a molar ratio of (1 to 1.25):1.

The reaction is carried out in the presence of a saturated aliphatic monocarboxylic acid as solvent. Care should here be taken to ensure that a sufficient amount of the aliphatic, saturated monocarboxylic acid is added. In general, the saturated, aliphatic monocarboxylic acid and the compound of the formula (II) are used in a weight ratio of (6 to 1.5):1.

The saturated, aliphatic monocarboxylic acid used as solvent is formic acid, acetic acid, propionic acid, n-butyric acid, i-butyric acid, n-valeric acid, i-valeric acid or mixtures of these acids. Particularly suitable solvents are acetic acid or propionic acid or mixtures thereof.

The reaction is carried out, as already mentioned in the introduction, at from 100° to 200° C. and in particular at from 115≅ to 160° C. The process is particularly simple if the reaction is carried out at the boiling point of the saturated aliphatic monocarboxylic acid or monocarboxylic acid mixture used in each case. Should this temperature be too low for carrying out the reaction, it is advisable to allow the reaction to proceed under superatmospheric pressure.

The present invention can be carried out either continuously or batchwise. It is particularly suitable for a batchwise method of operation.

The following examples illustrate the invention, without limiting it to them.

EXPERIMENTAL PART

EXAMPLE 1

Preparation of 2-(6H-dibenz-[c,e][1,2]-oxaphosphorinoxide-6-yl-methyl)succinic acid a) 151.2 g (0.7 mol) of 6H-dibenz-[c,e][1,2]-oxaphosphorin-6-one, 109.3 g (0.84 mol) of itaconic acid and 216.5 g of propionic acid are refluxed for 8 hours while stirring, then cooled and stirred further for 16 hours at room temperature. The precipitated crystalline product is subsequently filtered off with suction, washed and dried. This gives 222 g of the desired product having a melting point of 197° C. and a purity of 99.1% (determined by means of the $^{31}$P-NMR spectrum). This corresponds to a yield of 92% of theory, based on 6H-dibenz-[c,e][1,2]-oxaphosphorin-6-one.

b) 53.1 g (0.246 mol) of 6H-dibenz-[c,e][1,2]-oxaphosphorin-6-one, 32 g (0.246 mol) of itaconic acid and 75 ml of acetic acid are reacted in a 250 ml V4A autoclave for 8 hours at 150° C. and 1.5 bar. The mixture is then cooled, the autoclave discharged and the reaction solution formed is seeded by addition of seed crystals. Stirring is subsequently continued for a number of hours, the crystallized product formed is filtered off with suction, washed and dried.

This gives 70 g of the desired product having a melting point of from 189° to 193° C. This corresponds to a yield of 83% of theory.

COMPARATIVE EXAMPLE

Preparation of 2-(6H-dibenz-[c,e][1,2]-oxaphosphorinoxide-6-yl-methyl)succinic acid This comparative experiment corresponds to Example 1 of DE-C 28 16 100. 144 g (0.67 mol) of 6H-dibenz-[c,e][1,2]-oxaphosphorin-6-one (designated as 9,10-dihydro-9-oxa-10-phosphaphenanthrene 10-oxide in DE-C 28 16 100), 87 g (0.67 mol) of itaconic acid and 433 g of dimethyl sulfoxide are slowly heated while stirring. At the same time, nitrogen is slowly passed in through a gas inlet tube. However, as a result of, a rapidly commencing exothermic reaction, the temperature rises quickly and at 190° C. reaches reflux temperature. The heat evolution is so strong that the stirrer fitted is hardly sufficient to conduct away the heat liberated to a sufficient extent. After some minutes, refluxing abates and after 2 hours the reflux temperature is only from 150° to 165° C. Cooling gives a reaction mixture from which no crystals can be isolated.

EXAMPLE 2

Preparation of 2-(6H-dibenz-[c,e][1,2]-oxaphosphorinoxide-6-yl)succinic acid 43.2 g (0.2 mol) of 6H-dibenz-[c,e][1,2]-oxaphosphorin-6one, 23.2 g (0.2 mol) of fumaric acid and 95 g of propionic acid are refluxed for 20 hours with lively stirring, the mixture is then cooled and the propionic acid is distilled off in vacuo. The residue is digested with acetonitrile and the crystal mass formed is filtered off with suction. Purification is carried out by boiling out with water and subsequent drying. The desired product has a decomposition point of 219° C.

$C_{16}H_{13}O_6P$ (332) calc.: 57.8% C 3.92% H 9.34% P found: 57.8% C 3.9% H 9.0% P

EXAMPLE 3

Preparation of diphenylphosphinylmethylsuccinic acid 303 g (1.5 mol) of diphenylphosphine oxide, 214.5 g (1.65 mol) of itaconic acid and 470 g of propionic acid are refluxed under a nitrogen atmosphere for 8.5 hours with lively stirring. The mixture is then cooled. After crystallization, an additional 500 g of propionic acid are added, the product is filtered off with suction, washed and dried. This gives 390 g of product having a melting point of from 169° to 172° C. and a purity of 98.8% (determined by means of the $^{31}$P-NMR spectrum). A further 30 g of desired product are isolated from the filtrate. The total yield is 84% of theory, based on diphenylphosphine oxide used.

$C_{17}H_{17}O_5P$ (332) calc.: 61.45% C 5.12% H 9.34% P found: 61.5% C 5.2% H 8.9% P

EXAMPLE 4

Preparation of dimethylphosphinylmethylsuccinic acid 19.5 g (0.25 mol) of dimethylphosphine oxide, 35 g (0.27 mol) of itaconic acid and 77.5 g of propionic acid are refluxed under a nitrogen atmosphere for 7.5 hours with lively stirring. After cooling, the propionic acid is distilled off in vacuo and the residue is digested with 54 g of acetonitrile. This gives 26 g of the desired product having a melting point of from 138° to 143° C. This corresponds to a yield of 50% of theory.

We claim:

1. A process for preparing of phosphorus-containing dicarboxylic acids of the formula (I)

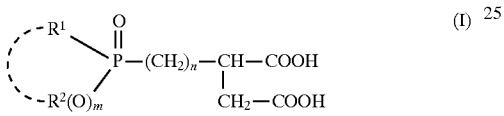

where $R^1$ and $R^2$ are identical or different and are each a straight-chain or branched alkyl radical having from 1 to 8 carbon atoms, a cycloaliphatic radical having 5 or 6 carbon atoms in the ring, an unsubstituted or substituted aryl radical having from 6 to 10 carbon atoms, or $R^1$ and $R^2$ form, with inclusion of the phosphorus atom, a ring having from 5 to 8 members, and m and n are each, independently of one another 0 or 1, which comprises reacting a compound of the formula (II)

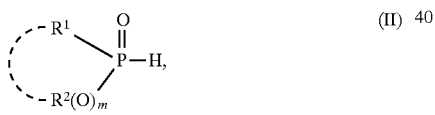

where $R^1$, $R^2$ and m are as defined above, with fumaric acid, maleic acid or itaconic acid in the presence of a saturated aliphatic monocarboxylic acid having a total of from 1 to 5 carbon atoms as solvent at from 100° to 200° C. under atmospheric pressure or superatmospheric pressure.

2. The process as claimed in claim 1, wherein the compound of the formula (II) used is one in which $R^1$ and $R^2$ form, with inclusion of the phosphorus atom, a ring having 6 or 7 members.

3. The process as claimed in claim 1, wherein the compound of the formula (II) used is one in which $R^1$ and $R^2$ are identical or different and are each a straight-chain or branched alkyl radical having from 1 to 4 carbon atoms, a cyclopentyl or cyclohexyl radical, an aryl radical which is substituted by one or more halogen, alkyl, alkoxy or aryl radicals, or $R^1$ and $R^2$ form, with inclusion of the phosphorus atom, an unsubstituted or substituted oxaphosphorin ring.

4. The process as claimed in claim 1, wherein the compound of the formula (II) used is one in which $R^1$ and $R^2$ are identical and are each a phenyl radical or a phenyl radical substituted by one or two alkyl groups or alkoxy groups and m=0.

5. The process as claimed in claim 1, wherein the compound of the formula (II) containing an oxaphosphorin ring which is used is a compound of the formula (III)

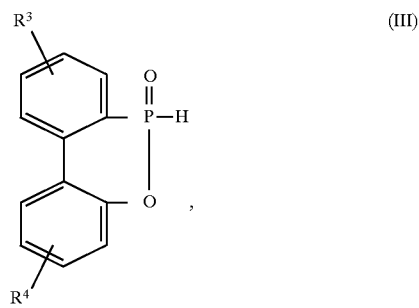

where $R^3$ and $R^4$ are identical or different and are each halogen, an alkyl radical having from 1 to 4 carbon atoms or an alkoxy radical having from 1 to 4 carbon atoms.

6. The process as claimed in claim 1, wherein the compound of the formula (II) used is 6H-dibenz-[c,e][1,2]-oxaphosphorin-6-one, dimethylphosphine oxide, methylpropylphosphine oxide, diisopropylphosphine oxide, di-n-butylphosphine oxide, methylphenylphosphine oxide, diphenylphosphine oxide or di-p-tolylphosphine oxide.

7. The process as claimed in claim 1, wherein the compound of the formula II is reacted with itaconic acid.

8. The process as claimed in claim 1, wherein the fumaric acid, maleic acid or itaconic acid and the compound of the formula (II) are used in a molar ratio of (1 to 1.25):1.

9. The process as claimed in claim 1, wherein the saturated aliphatic monocarboxylic acid and the compound of the formula (II) are used in a weight ratio of (6 to 1.5):1.

10. The process as claimed in claim 1, wherein the saturated aliphatic monocarboxylic acid used is acetic acid or propionic acid.

11. The process as claimed in claim 1, wherein the reaction is carried out at from 115° to 160° C.

* * * * *